(12) United States Patent
Gmeiner et al.

(10) Patent No.: US 7,645,877 B2
(45) Date of Patent: Jan. 12, 2010

(54) HEPTAZINE DERIVATIVES CONTAINING PHOSPHORUS, METHOD FOR THE PRODUCTION THEREOF AND USE THEREOF AS FLAME RETARDANTS

(75) Inventors: Tobias Gmeiner, Constance (DE); Edwin Kroke, Freiberg (DE); Marcus Schwarz, Freiberg (DE)

(73) Assignees: Zylum Beteiligungsgesellschaft mbH & Co., Schönefeld/Waltersdorf; Patente II KG (DE)

( * ) Notice: Subject to any disclaimer, the term of this patent is extended or adjusted under 35 U.S.C. 154(b) by 59 days.

(21) Appl. No.: 11/662,398

(22) PCT Filed: Sep. 14, 2005

(86) PCT No.: PCT/EP2005/009903

§ 371 (c)(1),
(2), (4) Date: Mar. 9, 2007

(87) PCT Pub. No.: WO2006/034784

PCT Pub. Date: Apr. 6, 2006

(65) Prior Publication Data

US 2008/0039624 A1      Feb. 14, 2008

(30) Foreign Application Priority Data

Sep. 29, 2004   (DE) .................. 10 2004 047 257

(51) Int. Cl.
*C07D 251/72* (2006.01)
*C07F 9/6561* (2006.01)
*C08K 5/5399* (2006.01)

(52) U.S. Cl. ................. 544/196; 544/198; 524/100; 524/139

(58) Field of Classification Search ............ 544/196, 544/198; 524/100, 139
See application file for complete search history.

(56) References Cited

U.S. PATENT DOCUMENTS 4,879,327 A   11/1989   Poisson et al.

FOREIGN PATENT DOCUMENTS

| CA | 2373013 A1 | 11/2000 |
|---|---|---|
| EP | 0994156 A1 | 4/2000 |
| WO | WO 98/24838 A1 | 6/1998 |
| WO | WO 00/66661 A1 | 11/2000 |

*Primary Examiner*—Venkataraman Balasubramanian
(74) *Attorney, Agent, or Firm*—McDonnell Boehnen Hulbert & Berghoff, LLP

(57) ABSTRACT

The present invention relates to unsymmetrical and symmetrical phosphorus-comprising heptazine derivatives, represented by the formula (1):

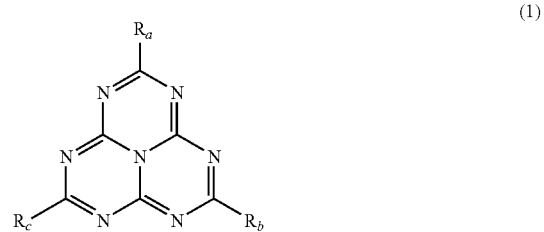

(1)

in which $R_a$, $R_b$ and $R_c$ are, independently of one another, an azide group —$N_3$ or an —N=$PR_1R_2R_3$ group, with the proviso that at least one radical from $R_a$, $R_b$ and $R_c$ is an —N=$PR_1R_2R_3$ group, to a process for the preparation thereof and to the use thereof.

10 Claims, No Drawings

HEPTAZINE DERIVATIVES CONTAINING PHOSPHORUS, METHOD FOR THE PRODUCTION THEREOF AND USE THEREOF AS FLAME RETARDANTS

The present invention relates to unsymmetrical and symmetrical phosphorus-comprising heptazine derivatives, represented by the formula (1):

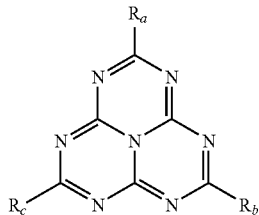

in which $R_a$, $R_b$ and $R_c$ are, independently of one another, an azide group —$N_3$ or an —N=$PR_1R_2R_3$ group, with the proviso that at least one radical from $R_a$, $R_b$ and $R_c$ is an —N=$PR_1R_2R_3$ group, to a process for the preparation thereof and to the use thereof.

It is known that numerous C/N/H compounds, especially s-triazine derivatives (in particular melamine and its derivatives), have flame-retardant properties. They are accordingly used in various fields as flame retardants. Typical applications are in the electronics, plastics, wood and textile industries, combustible materials being stabilized by the above compounds as flame retardants.

Furthermore, appropriate heptazine or tri-s-triazine derivatives, such as melem ($C_6H_6N_{10}$) and melon ($C_6H_3N_9$), are also suitable as, for example, plastic additives in fire-protecting applications.

Today, however, in many cases substances still comprising halogen are used as flame retardants. These are damaging to the health and pollute the environment. Accordingly, attempts have already been made, for a fairly long time, to replace them by halogen-free flame retardants. Phosphorus compounds are particularly promising and also occasionally used.

Recently, it has also been reported with regard to this that phosphorus and nitrogen, if they are present together in a polymer formulation, complement one another synergistically with regard to fire resistance.

It is accordingly an object of the present invention to make available novel compounds which are to be rich in nitrogen and phosphorus and preferably free from halogen and which are also to be suitable, inter alia, as flame retardants.

This object is achieved through the embodiments characterized in the claims.

In particular, unsymmetrical and symmetrical phosphorus-comprising heptazine derivatives, represented by the formula (1):

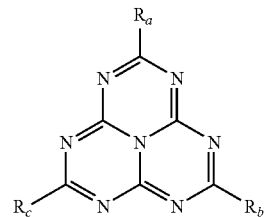

in which $R_a$, $R_b$ and $R_c$ are, independently of one another, an azide group —$N_3$ or an —N=$PR_1R_2R_3$ group, with the proviso that at least one radical from $R_a$, $R_b$ and $R_c$ is an —N=$PR_1R_2R_3$ group, and in which $R_1$, $R_2$ and $R_3$ are, independently of one another, a radical chosen from the group α consisting of a straight-chain or branched-chain $C_1$-$C_{12}$-alkyl radical, a $C_3$-$C_7$-cycloalkyl radical, a straight-chain or branched-chain $C_1$-$C_{12}$-alkenyl radical, a straight-chain or branched-chain $C_1$-$C_{12}$-alkoxy radical, furyl, furanyl, benzofuranyl, thienyl, thiazolyl, benzothiazolyl, thiadiazolyl, imidazolyl, pyrazolyl, triazolyl, tetrazolyl, pyrazinyl, benzothienyl, morpholinyl, thiomorpholinyl, piperidinyl, piperazinyl, pyrrolidinyl, pyrimidinyl, imidazolinyl, pyrazolidinyl, phenyl, phenoxy, benzyl, benzyloxy, naphthyl, naphthoxy, di($C_1$-$C_6$)alkylamino, tri($C_1$-$C_6$)alkylsilyl and pyridyl, which can in each case be substituted by one to five substituents chosen, independently of one another, from the group β consisting of a straight-chain or branched-chain $C_1$-$C_6$-alkyl radical, a $C_3$-$C_7$-cycloalkyl radical, a straight-chain or branched-chain $C_1$-$C_6$-alkenyl radical, a straight-chain or branched-chain $C_1$-$C_6$-alkoxy radical, halogen, hydroxy, amino, di($C_1$-$C_6$)alkylamino, nitro, cyano, benzyl, 4-methoxybenzyl, 4-nitrobenzyl, phenyl and 4-methoxyphenyl, and oligomers and polymers derived therefrom, are provided.

In a preferred embodiment of the present invention, symmetrical phosphorus-comprising heptazine derivatives, represented by the formula (2):

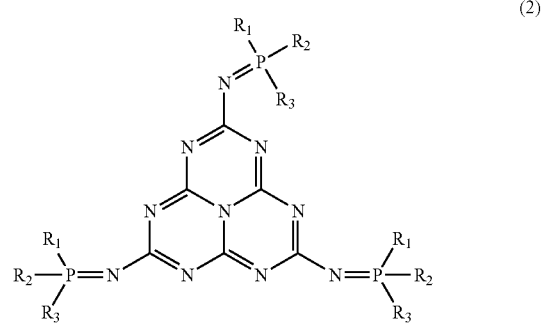

in which $R_1$, $R_2$ and $R_3$ are, independently of one another, a radical chosen from the group α consisting of a straight-chain or branched-chain $C_1$-$C_{12}$-alkyl radical, a $C_3$-$C_7$-cycloalkyl radical, a straight-chain or branched-chain $C_1$-$C_{12}$-alkenyl radical, a straight-chain or branched-chain $C_1$-$C_{12}$-alkoxy radical, furyl, furanyl, benzofuranyl, thienyl, thiazolyl, benzothiazolyl, thiadiazolyl, imidazolyl, pyrazolyl, triazolyl, tetrazolyl, pyrazinyl, benzothienyl, morpholinyl, thiomorpholinyl, piperidinyl, piperazinyl, pyrrolidinyl, pyrimidinyl, imidazolinyl, pyrazolidinyl, phenyl, phenoxy, benzyl, benzyloxy, naphthyl, naphthoxy, di($C_1$-$C_6$)alkylamino, tri($C_1$-$C_6$)

alkylsilyl and pyridyl, which can in each case be substituted by one to five substituents chosen, independently of one another, from the group β consisting of a straight-chain or branched-chain $C_1$-$C_6$-alkyl radical, a $C_3$-$C_7$-cycloalkyl radical, a straight-chain or branched-chain $C_1$-$C_6$-alkenyl radical, a straight-chain or branched-chain $C_1$-$C_6$-alkoxy radical, halogen, hydroxy, amino, di($C_1$-$C_6$)alkylamino, nitro, cyano, benzyl, 4-methoxybenzyl, 4-nitrobenzyl, phenyl and 4-methoxyphenyl, and oligomers and polymers derived therefrom, are provided.

Preferably, the group β comprises the above substituents exclusive of the halogens, i.e. no halogen substituents.

The phosphorus-comprising heptazine derivatives according to the invention are normally stable towards air and colorless.

In a particularly preferred embodiment of the present invention, $R_1$, $R_2$ and $R_3$ of the phosphorus-comprising heptazine derivative according to the above formula (1) or formula (2) are in each case a straight-chain or branched-chain $C_1$-$C_{12}$-alkyl radical, methyl or n-butyl being particularly preferred for $R_1$, $R_2$ and $R_3$.

In another particularly preferred embodiment of the present invention, $R_1$, $R_2$ and $R_3$ of the phosphorus-comprising heptazine derivative according to the above formula (1) or formula (2) are in each case phenyl or in each case m-cresyl.

In comparison with the conventional flame retardants of the state of the art, the phosphorus-comprising heptazine derivatives according to the invention, which also can be described as melemphosphoranylides, can advantageously be varied, with regard to the physical and chemical properties of the resulting compounds of this family, by appropriate choice of the radicals and thus in a simple way can be targeted in a "tailor-made" fashion at a particular application.

With regard to a use of the phosphorus-comprising heptazine derivatives according to the invention as flame retardants, an increased solubility of the derivative in a plastic to be protected and better adaptation to the application requirements, for example, can thus advantageously be targeted. The family of the phosphorus-comprising heptazine derivatives according to the invention already exhibits, on the basis alone of its chemical structure, a better solubility in plastics than melon and melem, which have to be used as solids and, for application as flame retardants, have to be especially reduced in size.

Furthermore, the phosphorus-comprising heptazine derivatives according to the invention exhibit the advantage that they, with regard to a flame-retardant use, can be fashioned to be halogen-free with regard to the radicals $R_1$, $R_2$ and $R_3$ and accordingly, in comparison with the halogen-comprising flame retardants of the state of the art, are environmentally friendly.

According to an additional embodiment of the present invention, the phosphorus-comprising heptazine derivatives can also be present as oligomer or polymer, structural units being present in the latter, for example, which carry two or more bridging phosphine groups or phosphazene bridgings, so that two or more heptazine units are connected to one another, as shown by way of example in the following formula (3):

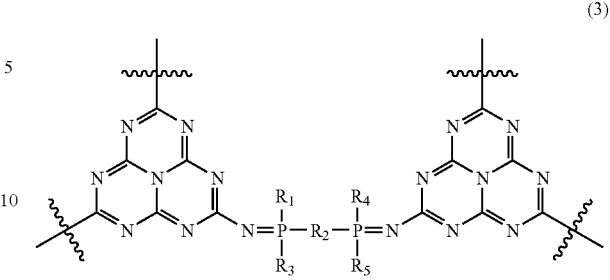

(3)

An additional subject matter of the present invention is a process for the preparation of the unsymmetrical or symmetrical phosphorus-comprising heptazine derivatives according to the formula (1) defined above, which comprises the stage of the reaction of triazidotri-s-triazine ($C_6N_{16}$) with at least one equivalent of a phosphine $PR_1R_2R_3$ in a Staudinger reaction, in which $R_1$, $R_2$ and $R_3$ are as defined above. Symmetrical phosphorus-comprising heptazine derivatives according to the formula (2) can correspondingly be prepared by the reaction of triazidotri-s-triazine ($C_6N_{16}$) with at least three equivalents of a phosphine $PR_1R_2R_3$ in a Staudinger reaction. Naturally, in the context of the present invention, the reaction can also be carried out with an appropriate mixture of phosphines.

It has been established that phosphorus-comprising heptazine derivatives of the formula (1) or (2) according to the present invention can be synthesized in a simple way from triazinotri-s-triazine ($C_6N_{16}$) via a Staudinger reaction. The products are obtained in high yields and can be satisfactorily purified.

The solvent to be used in the process according to the invention is not subject to any specific limitation. Polar aprotic solvents or solvent mixtures are normally used for this. The solvent is preferably chosen from the group consisting of dimethyl sulfoxide (DMSO), dimethylformamide (DMF), tetrahydrofuran (THF), dioxane, acetonitrile and pyridine. DMSO is particularly preferably used as solvent in the process according to the invention.

In the process according to the invention, the nitrogen gas released in a polycondensation by reaction of triazidotri-s-triazine with a compound carrying two or more phosphine groups can advantageously act at the same time as blowing agent, so that in this way polymer foams can also be produced.

Alternatively, the compounds according to the invention can also be obtained in a two-stage process by reaction of melem with phosphorus pentachloride in phosphorus oxychloride, with $C_6N_7(N=PCl_3)_3$ being obtained as intermediate which can be used for multivarious purposes, and subsequent reaction of this intermediate with compounds of the X—OH type, X then being an alkyl, aryl or heterocycle radical defined above, with nucleophilic substitution of one or more chlorine atoms, or reaction of the —N=$PCl_3$ group with appropriate organometallic compounds, such as, e.g., Grignard reagents, such as X—MgHal, and Li—X.

An additional subject matter of the present invention is the use of the phosphorus-comprising heptazine derivatives according to the formula (1) or (2) defined above as flame retardant, in particular for plastics, textiles, wood products, paper, cardboard articles, plaster, insulating materials and building material composites.

In addition, the phosphorus-comprising heptazine derivatives according to the present invention can also, however, be used for the preparation of materials in which optical, acoustic, magnetic or (opto)electronic properties of the derivatives according to the invention are used. In such a case, it can then also be possible for the phosphorus-comprising heptazine derivative according to the invention to comprise halogen atoms.

Furthermore, the phosphorus-comprising heptazine derivatives according to the present invention can also be used for the preparation of polymer foams, as already referred to.

The present invention is illustrated further by the following nonlimiting examples.

EXAMPLES

All reactions were carried out under a protective gas using the Schlenk and glovebox technique. Commercially available (Aldrich) starting materials were used. Triazidotri-s-triazine ($C_6N_{16}$) was synthesized according to a literature procedure.

The general reaction of the following examples 1 to 4 proceeds as follows:

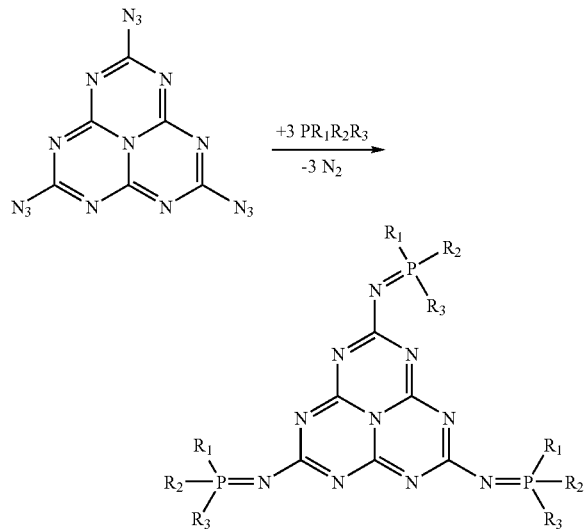

Example 1

$R_1=R_2=R_3=Ph$ 65 mg (0.22 mol) of pure triazide were dissolved in dry DMSO in a Schlenk flask (50 ml) with a magnetic stirrer bar. A total of 190 mg (0.72 mmol) of pulverized $P(Ph)_3$ dried beforehand over $P_4O_{10}$ was added in small portions to the solution with stirring. The $P(Ph)_3$ went completely into solution in the course of this, it being possible to observe a slight evolution of gas and a more intense yellow coloring of the reaction mixture. The reaction mixture became cloudy after approximately 30 min. After stirring at ambient temperature for an additional 1 h, a white precipitate was obtained. The suspension was centrifuged and the supernatant solution was decantered off. The residual solid was dried under vacuum at 80° C. and the absence of solvent was verified by means of IR spectra. White solid, yield: 145 mg (66%, based on the $C_6N_{16}$ used). FT-IR (KBr, cm$^{-1}$): 1620 (vs), 1393 (vs), 1273 (s), 1182 (m), 1109 (s), 1037 (m), 926 (m), 720 (m), 533 (m). MS (MALDI, m/z) 999.7 (M+H$^+$), 739.5 (M$^+$–PPh$_3$+3H). Observations on heating: 210-215° C. yellow coloring, from 230° C. brown product, the IR spectrum of which is identical with the heptazine derivative synthesized.

Example 2

$R_1=R_2=R_3=Me$ 0.5 ml of $P(Me)_3$ was placed in a single-necked Schlenk flask (50 ml) with a magnetic stirrer bar. A solution of 440 mg (1.5 mmol) of $C_6N_{16}$ in 10 ml of dry DMSO was slowly added dropwise to this at ambient temperature. In the course of this, vigorous evolution of gas and warming of the reaction mixture occurred. After that, the reaction mixture was cooled in a water bath to just short of the freezing point of DMSO. After adding dropwise approximately half of the $C_6N_{16}$ solution, no further decoloring of the same occurred. After addition of the total amount of $C_6N_{16}$, the solution was concentrated under vacuum and freed from volatile constituents at 80-90° C.

Example 3

$R_1=R_2=R_3=$n-butyl 0.85 ml (3.4 mmol) of tri(n-butyl)phosphine was placed in a Schlenk flask (50 ml) with a magnetic stirrer bar. A solution of 300 mg (1 mmol) of $C_6N_{16}$ in approximately 10 ml of dry DMSO was slowly added dropwise to this at ambient temperature. In the course of this, the solution changed to orange-yellow in color with slight evolution of gas and became light-yellow after additional stirring. The mixture was stirred overnight. In this connection, phase separation into an off-white suspension over a yellowish solution occurred. A white solid was obtained by filtering through a sintered glass funnel under a protective gas. The solid was washed with a small amount of DMSO and subsequently dried under vacuum. The residual substance (533 mg, 65%, based on $C_6N_{16}$) was recrystallized from THF. Clear colorless crystals were produced which, without surrounding solvent, quickly became cloudy. MS (MALDI, m/z) 619.6 (M$^+$–P(n-Bu)$_3$+3H); 419.2 (M$^+$–2P(n-Bu)$_3$+5H).

Example 4

$R_1=R_2=R_3=$m-cresyl 1.25 ml of tri(m-cresyl)phosphine were placed in a Schlenk flask (50 ml) with a magnetic stirrer bar. A solution of 300 mg (1 mmol) of $C_6N_{16}$ in approximately 10 ml of dry DMSO was slowly added dropwise to this at ambient temperature. In the course of this, slight warming and weak evolution of gas were observed. The reaction mixture was stirred overnight and then the solvent was evaporated off under vacuum. The residual yellow-brown oil was dissolved in THF and heated to reflux. In the course of this, a beige precipitate was obtained, which was filtered off and dried in air, giving a yield of 142 mg.

Observations on heating ("melting point determination"): from 178° C. dark-brown discoloration, furthermore no change up to 340° C. It could be proved, by means of IR spectroscopy, that traces of the triazide starting compound are responsible for the discoloration. The absence of any further change up to 380° C. is evidence for the high thermal stability of the phosphorus-comprising heptazine derivative obtained.

Example 5

Preparation of the Intermediate $C_6N_7(N=PCl_3)_3$

Melem washed with hot distilled water and dried under vacuum (1.00 g, 4.58 mmol) is suspended with $PCl_5$ in $POCl_3$ under a protective gas. This yellow-brown suspension is heated at reflux with stirring for 20 h, a bulky white solid being formed. The product is freed from excess $PCl_5$ and $POCl_3$ by centrifuging off and washing repeatedly with dry pentane. Elemental analysis and mass spectra confirm the formation of $C_6N_7(N=PCl_3)_3$.

What is claimed is:

1. A compound represented by the formula (1):

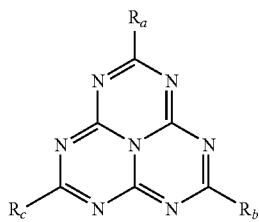

in which $R_a$, $R_b$ and $R_c$ are, independently of one another, an azide group —$N_3$ or an —$N=PR_1R_2R_3$ group, with the proviso that at least one radical from $R_a$, $R_b$ and $R_c$ is an —$N=PR_1R_2R_3$ group, and in which $R_1$, $R_2$ and $R_3$ are, independently of one another, a radical chosen from the group α consisting of a straight-chain or branched-chain $C_1$-$C_{12}$-alkyl radical, a $C_3$-$C_7$-cycloalkyl radical, a straight-chain or branched-chain $C_2$-$C_{12}$-alkenyl radical, a straight-chain or branched-chain $C_1$-$C_{12}$-alkoxy radical, furyl, furanyl, benzofuranyl, thienyl, thiazolyl, benzothiazolyl, thiadiazolyl, imidazolyl, pyrazolyl, triazolyl, tetrazolyl, pyrazinyl, benzothienyl, morpholinyl, thiomorpholinyl, piperidinyl, piperazinyl, pyrrolidinyl, pyrimidinyl, imidazolinyl, pyrazolidinyl, phenyl, phenoxy, benzyl, benzyloxy, naphthyl, naphthoxy, di($C_1$-$C_6$)alkylamino, tri($C_1$-$C_6$)alkylsilyl and pyridyl, which can in each case be further substituted by one to five substituents chosen, independently of one another, from the group β consisting of a straight-chain or branched-chain $C_1$-$C_6$-alkyl radical, a $C_3$-$C_7$-cycloalkyl radical, a straight-chain or branched-chain $C_2$-$C_6$-alkenyl radical, a straight-chain or branched-chain $C_1$-$C_6$-alkoxy radical, halogen, hydroxy, amino, di($C_1$-$C_6$)alkylamino, nitro, cyano, benzyl, 4-methoxybenzyl, 4-nitrobenzyl, phenyl and 4-methoxyphenyl.

2. The compound as claimed in claim 1, represented by the formula (2):

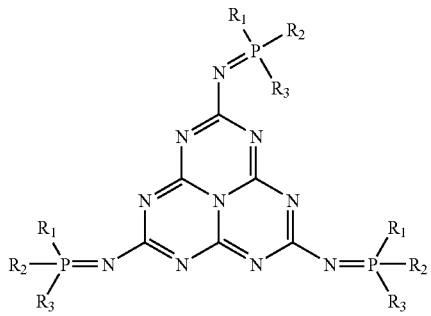

in which $R_1$, $R_2$ and $R_3$ are, independently of one another, a radical chosen from the group α consisting of a straight-chain or branched-chain $C_1$-$C_{12}$-alkyl radical, a $C_3$-$C_7$-cycloalkyl radical, a straight-chain or branched-chain $C_2$-$C_{12}$-alkenyl radical, a straight-chain or branched-chain $C_1$-$C_{12}$-alkoxy radical, furyl, furanyl, benzofuranyl, thienyl, thiazolyl, benzothiazolyl, thiadiazolyl, imidazolyl, pyrazolyl, triazolyl, tetrazolyl, pyrazinyl, benzothienyl, morpholinyl, thiomorpholinyl, piperidinyl, piperazinyl, pyrrolidinyl, pyrimidinyl, imidazolinyl, pyrazolidinyl, phenyl, phenoxy, benzyl, benzyloxy, naphthyl, naphthoxy, di($C_1$-$C_6$)alkylamino, tri($C_1$-$C_6$)alkylsilyl and pyridyl, which can in each case be further substituted by one to five substituents chosen, independently of one another, from the group β consisting of a straight-chain or branched-chain $C_1$-$C_6$-alkyl radical, a $C_3$-$C_7$-cycloalkyl radical, a straight-chain or branched-chain $C_2$-$C_6$-alkenyl radical, a straight-chain or branched-chain $C_1$-$C_6$-alkoxy radical, halogen, hydroxy, amino, di($C_1$-$C_6$)alkylamino, nitro, cyano, benzyl, 4-methoxybenzyl, 4-nitrobenzyl, phenyl and 4-methoxyphenyl.

3. The compound as claimed in any of claims 1 or 2, in which $R_1$, $R_2$ and $R_3$ are in each case a straight-chain or branched-chain $C_1$-$C_{12}$-alkyl radical.

4. The compound as claimed in any of claims 1 or 2, $R_1$, $R_2$ and $R_3$ being in each case methyl or in each case n-butyl.

5. The compound as claimed in any of claims 1 or 2, $R_1$, $R_2$ and $R_3$ being in each case phenyl or in each case m-cresyl.

6. A process for the preparation of a compound according to the formula (1) as claimed in claim 1, which comprises the stage of the reaction of triazidotri-s-triazine ($C_6N_{16}$) with at least one equivalent of a phosphine $PR_1R_2R_3$ in a Staudinger reaction.

7. A process for the preparation of a compound according to the formula (2) as claimed in claim 2, which comprises the stage of the reaction of triazidotri-s-triazine ($C_6N_{16}$) with at least three equivalents of a phosphine $PR_1R_2R_3$ in a Staudinger reaction.

8. A process for the preparation of a compound according to the formula (2), which comprises:
    reacting melem with phosphorus pentachloride in phosphorus oxychloride to produce $C_6N_7(N=PCl_3)_3$ as an intermediate; and
    reacting the intermediate with either compounds of the X—OH type or an organic metallic compound X—MgHal or Li—X to produce the compound according to formula (2), wherein X represents a radical chosen from the group α consisting of a straight-chain or branched-chain $C_1$-$C_{12}$-alkyl radical, a $C_3$-$C_7$-cycloalkyl radical, furyl, furanyl, benzofuranyl, thienyl, thiazolyl, benzothiazolyl, thiadiazolyl, imidazolyl, pyrazolyl, triazolyl, tetrazolyl, pyrazinyl, benzothienyl, morpholinyl, thiomorpholinyl, piperidinyl, piperazinyl, pyrrolidinyl, pyrimidinyl, imidazolinyl, pyrazolidinyl, phenyl, phenoxy, benzyl, benzyloxy, naphthyl, naphthoxy, di($C_1$-$C_6$)alkylamino, tri($C_1$-$C_6$)alkylsilyl and pyridyl, which can in each case be further substituted by one to five substituents chosen, independently of one another, from the group β consisting of a straight-chain or branched-chain $C_1$-$C_6$-alkyl radical, a $C_3$-$C_7$-cycloalkyl radical, a straight-chain or branched-chain $C_2$-$C_6$-alkenyl radical, a straight-chain or branched-chain $C_1$-$C_6$-alkoxy radical, halogen, hydroxy, ammo, di($C_1$-$C_6$)alkylamino, nitro, cyano, benzyl, 4-methoxybenzyl, 4-nitrobenzyl, phenyl and 4-methoxyphenyl.

9. An article of manufacture comprising the compound according to the formula (1) or (2) as claimed in any of claims 1 or 2.

10. The article of manufacture according to claim 9, wherein said article of manufacture comprises plastics, textiles, wood products, paper, cardboard articles, plaster, insulating materials, building material composites, or polymer foams.

* * * * *